United States Patent
Huang et al.

(10) Patent No.: US 6,812,179 B2
(45) Date of Patent: Nov. 2, 2004

(54) PROCESS FOR REGENERATING A SLURRY FISCHER-TROPSCH CATALYST

(75) Inventors: Jui-Hsin R. Huang, Tulsa, OK (US); Kenneth L. Agee, Bixby, OK (US); Kym B. Arcuri, Tulsa, OK (US); Paul F. Schubert, Bartlesville, OK (US)

(73) Assignee: Syntroleum Corporation, Tulsa, OK (US)

(*) Notice: Subject to any disclaimer, the term of this patent is extended or adjusted under 35 U.S.C. 154(b) by 172 days.

(21) Appl. No.: 10/121,255

(22) Filed: Apr. 12, 2002

(65) Prior Publication Data

US 2002/0183403 A1 Dec. 5, 2002

Related U.S. Application Data

(60) Provisional application No. 60/286,411, filed on Apr. 25, 2001.

(51) Int. Cl.[7] ................................. B01J 20/34
(52) U.S. Cl. .................................. 502/41
(58) Field of Search ................. 502/38, 41, 45, 502/49

(56) References Cited

U.S. PATENT DOCUMENTS

| | | |
|---|---|---|
| 2,159,140 A | 5/1939 | Eckell et al. |
| 2,238,726 A | 4/1941 | Feisst et al. |
| 2,247,087 A | 6/1941 | Herbert |
| 2,259,961 A | 10/1941 | Mydleton |
| 2,289,731 A | 7/1942 | Roelen et al. |
| 2,440,109 A | 4/1948 | Moore |
| 2,458,870 A | 1/1949 | Ogorzaly |
| 2,498,845 A | 2/1950 | Smith et al. |
| 2,615,911 A | 10/1952 | Williams |
| 4,052,477 A | 10/1977 | Ireland et al. |
| 4,729,981 A | 3/1988 | Kobylinski et al. |
| 5,260,239 A | 11/1993 | Hsia |
| 5,348,982 A | 9/1994 | Herbolzheimer et al. |
| 5,543,437 A | 8/1996 | Benham et al. |
| 5,545,674 A | 8/1996 | Behrmann et al. |
| 5,811,363 A | 9/1998 | Leviness et al. |
| 5,811,468 A | 9/1998 | Chang et al. |
| 5,817,702 A | 10/1998 | Behrmann et al. |
| 5,821,270 A | 10/1998 | Chang et al. |
| 5,844,005 A | 12/1998 | Bauman et al. |
| 6,022,755 A | 2/2000 | Kinnari et al. |
| 6,100,304 A | 8/2000 | Singleton et al. |
| 6,255,358 B1 | 7/2001 | Singleton et al. |
| 6,284,807 B1 | 9/2001 | Leviness et al. |
| 6,323,248 B1 | 11/2001 | Mart et al. |

Primary Examiner—Stanley S. Silverman
Assistant Examiner—Edward M. Johnson
(74) Attorney, Agent, or Firm—Jenkens & Gilchrist, P.C.

(57) ABSTRACT

A process for regenerating a slurry Fischer-Tropsch catalyst, which needs regeneration, involves de-waxing and drying the catalyst sufficiently to produce a free-flowing catalyst powder that is fluidizable; fluidizing the catalyst powder; treating the catalyst powder with an oxygen treatment; reducing the catalyst powder with a reducing gas to form a reduced catalyst powder; and mixing the reduced catalyst powder with hydrocarbons to form a regenerated, slurry catalyst. The oxidation and reduction steps may be repeated. An oxygen treatment includes using a fixed $O_2$ level with ramped temperatures, fixed temperatures with increased $O_2$ levels, or a combination.

24 Claims, 3 Drawing Sheets

PROCESS FOR REGENERATING A SLURRY FISCHER-TROPSCH CATALYST

RELATED PATENT APPLICATION

This application claims priority of U.S. Provisional Application No. 60/286,411, filed Apr. 25, 2001, entitled, "Process for regenerating a slurry Fischer-Tropsch catalyst."

TECHNICAL FIELD OF THE INVENTION

The present invention relates to hydrocarbon conversion systems, such as Fischer-Tropsch gas-to-liquids plants, and more particularly to a process for regenerating a slurry, conversion catalyst.

BACKGROUND OF THE INVENTION

The commercial incentives for a process to convert synthesis gas to liquid fuels and other products are increasing as the need for energy sources increases. One successful approach to meeting this need has been to make synthesis gas and then synthetically convert the synthesis gas into heavier hydrocarbons ($C_{5+}$) through the Fischer-Tropsch (F-T) process. The synthetic production of hydrocarbons by the catalytic reaction of synthesis gas is well known and is generally referred to as the Fischer-Tropsch reaction. This process was developed nearly eighty years ago in Germany, and since then, it has been practiced commercially in Germany during World War II and later in South Africa.

Fischer-Tropsch hydrocarbon conversion systems typically have a synthesis gas generator and a Fischer-Tropsch reactor unit. In the case of starting with a gas feed stock, the synthesis gas generator receives light, short-chain hydrocarbons such as methane and produces synthesis gas. The synthesis gas is then delivered to a Fischer-Tropsch reactor. In the F-T reactor, the synthesis gas is primarily converted to useful $C_{5+}$ hydrocarbons. Recent examples of Fischer-Tropsch systems are included in U.S. Pat. Nos. 4,883,170; 4,973,453; 5,733,941; and 5,861,441, all of which are incorporated by reference herein for all purposes.

Numerous types of reactor systems have been used for carrying out the Fischer-Tropsch reaction. See generally the many examples found on www.fischertropsch.org. The commercial development of the Fischer-Tropsch reactor systems has included conventional fixed-bed and three-phase slurry bubble column designs or other moving-bed designs. But, due to the complicated interplay between heat and mass transfer and the relatively high cost of Fischer-Tropsch catalysts, no single reactor design has dominated the commercial developments to date.

Fischer-Tropsch three-phase bubble column reactors or the like appear to offer distinct advantages over the fixed-bed design in terms of heat transfer and diffusion characteristics. One particular type of three-phase bubble column is the slurry bubble column, wherein the catalyst size is generally between 10 and 200 microns ($\mu M$). Three-phase bubble column reactors present a number of technical challenges.

The technical challenges associated with three-phase bubble columns include solids management. One particular challenge in this area is to efficiently rejuvenate slurry catalysts. When a slurry Fischer-Tropsch catalyst is used over time, it has a disadvantage of slowly, but reversibly, deactivating compared to its initial catalytic activity. As the synthesis gas (primarily $H_2$ and CO) is fed to the Fischer-Tropsch reactor and converted with the F-T catalyst, the catalyst experiences deactivation caused by carbon build up, physical degradation, and the effects of trace compounds other than CO and $H_2$, such as by nitrogen containing species or oxygenated byproducts. "Carbon build up" references the accumulation of heavy hydrocarbons and carbonaceous type material that can have a hydrogen content less than that of F-T products. To remedy the deactivation, the catalyst is regenerated, or rejuvenated, using any of a number of techniques.

Rejuvenation is different from the initial activation of the Fischer-Tropsch catalyst. For cobalt catalysts, the initial activation involves converting the cobalt to a reduced state. An example of an initial activation technique is found U.S. Pat. No. 4,729,981, entitled "ROR-Activated Catalyst for Synthesis Gas Conversion," which describes the initial preparation of a cobalt or nickel based Fischer-Tropsch catalyst by reducing it in hydrogen, oxidizing it in an oxygen-containing gas, and then reducing it in hydrogen. The catalyst is then ready for its initial use. Once in use, it will begin to deactivate, and it will need regeneration.

Regeneration of a Fischer-Tropsch catalyst after activation and operation has long been known to restore the activity of the catalyst. See, e.g., H. H. Storch et al., *The Fischer-Tropsch And Related Synthesis* (Wiley: New York 1951), 211–222. Storch describes using hydrogen treatments to restore the catalyst activity. There are many other examples. For example, U.S. Pat. No. 2,159,140 describes pulling the catalyst from the reactor (where it appears to have been fluidized) and removing the catalyst and treating it with hydrogen to regenerate the catalyst. U.S. Pat. No. 2,238,726 indicates that the non-volatile reaction products can be removed from the catalyst by treating it with hydrogen or gases or vapors containing hydrogen and that this can be done in the midst of oil circulation. Col. 2:34–54. As another example, U.S. Pat. No. 2,616,911 describes oxidizing the catalyst and then reducing it while maintaining it in suspension or a fluidized state. Other examples relating to regenerating and/or de-waxing Fischer-Tropsch catalysts include U.S. Pat. Nos. 6,323,248 B1; 6,201,030 B1; 5,844,005; 5,292,705; 2,247,087; 2,259,961; 2,289,731; 2,458,870; 2,518,337; and 2,440,109.

Regenerating a slurry catalyst presents particular challenges because the catalyst is in slurry form. Elaborate efforts have been made to separate the catalyst to allow regeneration outside the Fischer-Tropsch reactor or to regenerate it in-situ. The rejuvenation can be carried out intermittently or continuously.

As an example of a regeneration process, U.S. Pat. No. 5,973,012 describes a reversibly deactivated, particulate slurry catalyst that is rejuvenated by circulating the slurry from a slurry body through (i) a gas disengaging zone to remove gas bubbles from the slurry, (ii) a catalyst rejuvenation zone in which a catalyst rejuvenating gas contacts the catalyst in the slurry to rejuvenate it and to form a rejuvenated catalyst slurry, and (iii) a means for returning catalyst to the slurry body. This design appears to be primarily for use as in-situ regeneration design. The "in-situ" regeneration offers the advantage of keeping the catalyst in the slurry matrix; however, it presents many challenges. Amongst other challenges in-situ regeneration, the $H_2$ partial pressure in the process is limited due to the low solubility of $H_2$ in the liquid phase. Typically, the $H_2$ partial pressure exposed to the catalyst within the liquid phase is less than about 10% of that in the gas phase. In addition, the hydrogen used to regenerate may modify the $H_2$:CO ratio in the reactor for some time. Further still, the temperature may be limited by the boiling point and/or cracking properties of the liquid slurry constituents. For these reasons, "in situ" regeneration has real limitations.

SUMMARY OF THE INVENTION

Therefore, a need has arisen for a process and system for regenerating a slurry Fischer-Tropsch catalyst that addresses shortcomings of previous techniques and systems. According to an aspect of the present invention, a process for converting light hydrocarbons into heavier hydrocarbons (C5+) includes the steps of: preparing a synthesis gas using light hydrocarbons; converting the synthesis gas to Fischer-Tropsch products in a slurry Fischer-Tropsch reactor containing a slurry Fischer-Tropsch catalyst; removing Fischer-Tropsch products from the slurry Fischer-Tropsch reactor; regenerating the slurry Fischer-Tropsch catalyst by de-waxing and drying the catalyst sufficiently to produce a free-flowing catalyst powder that is fluidizable; fluidizing the catalyst powder; treating the catalyst powder with an oxygen treatment to remove hydrocarbons from the catalyst powder; reducing the catalyst powder with a reducing gas, re-slurring the catalyst powder to form a regenerated slurry catalyst; and returning the regenerated slurry catalyst to the slurry Fischer-Tropsch reactor.

According to another aspect of the present invention, a process for regenerating a slurry Fischer-Tropsch catalyst includes the steps of: de-waxing and drying the catalyst sufficiently to produce a free-flowing catalyst powder that is fluidizable; fluidizing the catalyst powder; treating the catalyst powder with an oxygen treatment to remove residual hydrocarbons and/or carbonaceous material from the catalyst powder while re-oxidizing the catalyst; reducing the catalyst powder with a reducing gas to form a reduced catalyst powder; and mixing the reduced catalyst powder with hydrocarbons to form a regenerated, slurry catalyst. The oxygen level in the oxygen treatment may be varied or held constant or a combination approach used. The $CO_2$ off gas may be monitored to determine when a sufficient amount of hydrocarbons have been removed from the catalyst.

The present invention provides advantages; a number of examples follow. An advantage of the present invention, in one embodiment, is that a slurry F-T catalyst is separated before regeneration. An advantage is that the regeneration process presented avoids some of the disadvantages of in-situ regeneration. Another advantage is that additional product is recovered. Another advantage is that the slurry F-T catalyst may be regenerated continuously or in batches. Yet another advantage is that full activity may be maintained for extended periods of time. Another advantage is that the regeneration process of the present invention offers the flexibility to treat deactivated catalyst over a wide range of temperatures and $H_2$ partial pressures. It is an advantage that catalyst activity may be restored to levels of activity approaching that of a fresh catalyst regardless of the activity of the catalyst needing regeneration.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

Figure 1:
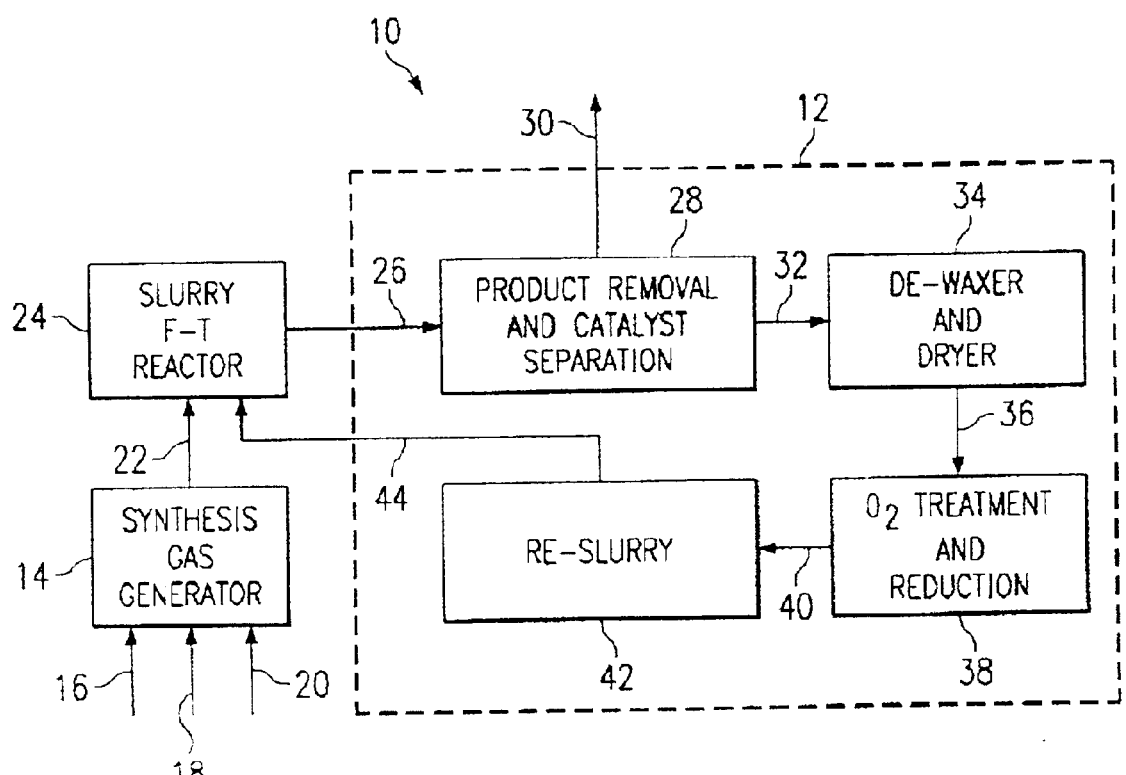
FIG. 1 is a schematic diagram of one embodiment according to the present invention.
Figure 2:
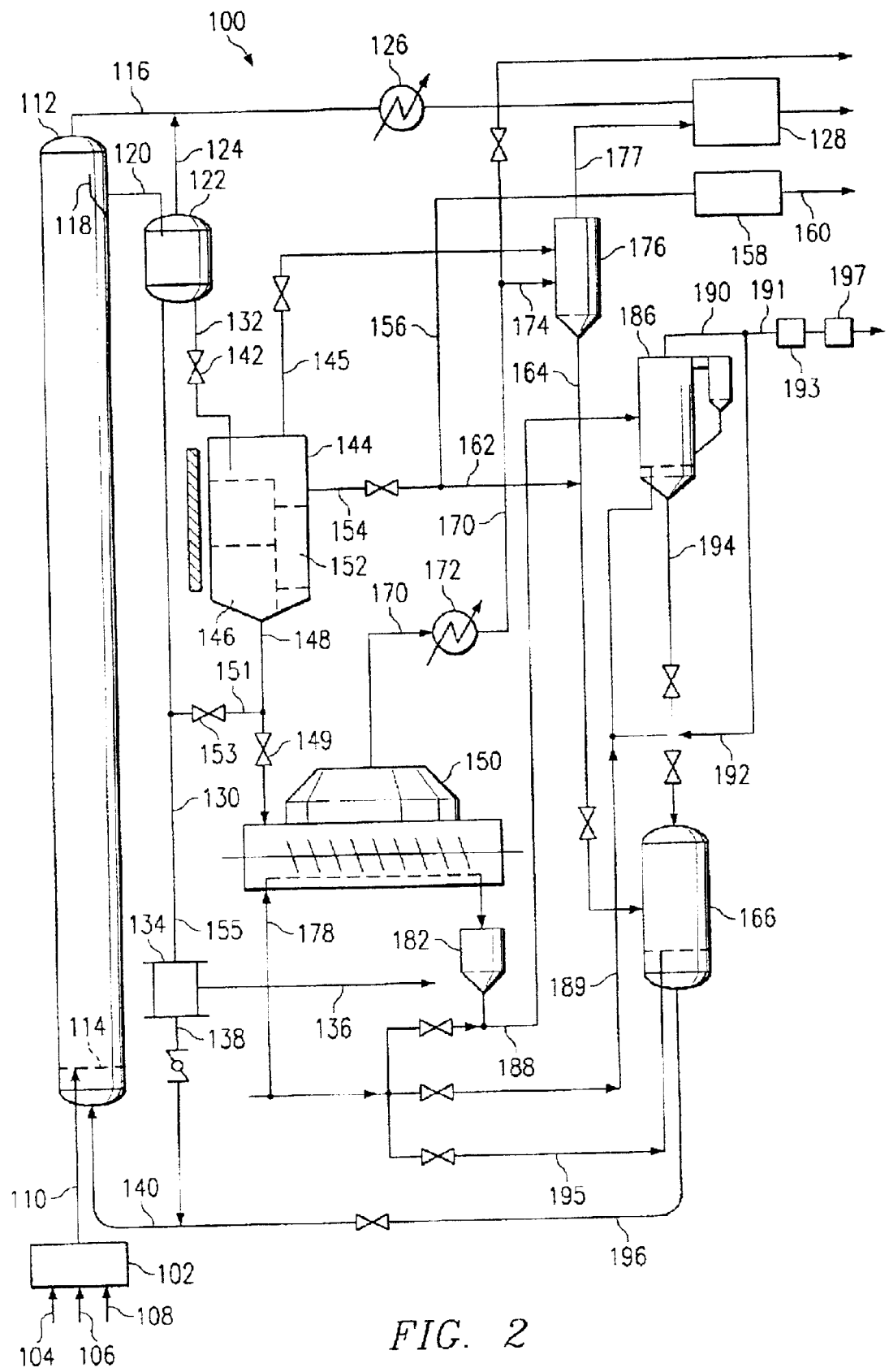
FIG. 2 is a schematic diagram of another embodiment according to the present invention.

The preferred embodiment of the present invention and its advantages are best understood by referring to FIGS. 1–2 of the drawings, like numerals being used for like and corresponding parts of the various drawings.

Referring to FIG. 1, a system 10 for converting light hydrocarbons, such as natural gas, to heavier hydrocarbons ($C_{5+}$) is presented that importantly includes a slurry Fischer-Tropsch catalyst regeneration subsystem 12. The process and system are applicable to all Fischer-Tropsch catalyst systems that are deactivated through use, such as by heavy hydrocarbons deposits or carbonaceous material deposits, oxidation of active sites, and/or agglomeration of active surface area, and therefore need to be regenerated. In a moving-bed system, there exists an age population for the catalyst converting synthesis gas into products, and the composite catalyst activity should be held at an acceptable level for the desired liquid products to be produced. Typically this will require regeneration when the activity drops 5–10 percent from the initial activity level. As used herein, a "catalyst in need of regeneration" refers to a catalyst that has experienced a loss of more than about 10 percent, and more preferably 5–10 percent, of its initial activity. Note that in addition to Fischer-Tropsch, this process may have application in other hydrocarbon conversion systems.

An overview of system 10 is provided and then aspects of it will be explained in more detail further below. Synthesis gas generator 14 receives light hydrocarbons 16 (e.g., methane), steam 18, and an oxygen-containing gas 20 (e.g., air) and produces a synthesis gas 22. Synthesis gas generator 14 can be any of numerous types of synthesis gas generators such as an autothermal reformer (ATR) reactor, steam methane reformer (SMR), or a partial oxidation unit (POX). Alternatively, the synthesis gas could be generated by gasifying solid carbonaceous material such as coal.

A slurry Fischer-Tropsch reactor 24 receives the synthesis gas 22 and converts it to Fischer-Tropsch products. The slurry reactor 24 can be any of a number of embodiments, but features a three-phase system that has a slurry Fischer-Tropsch catalyst that is between 5 and 250 $\mu$M, and more preferably, between 10 and 100 $\mu$M. The catalyst matrix as used may also include small particles (e.g., less than 5 microns) due to attrition or residual fines from the manufacturing process. The Fischer-Tropsch catalyst usually is based on a supported Group VIII metal, such as a cobalt-based catalyst that may be on a suitable support (e.g., alumina, titania, silica, etc.). To successfully operate system 10, two items need to be removed from the slurry Fischer-Tropsch reactor 24: the Fischer-Tropsch products and the slurry catalyst that is to be regenerated. This is figuratively shown by the stream 26 going to product-removal-and-catalyst-separation unit 28. Stream 30 represents the F-T products that have been separated and taken to storage, upgrading, or for use elsewhere as part of system 10. The slurry F-T catalyst (which may initially be about 5–45 wt. % catalyst in the slurry) is concentrated, or separated, (preferably concentrated to at least 50 wt. % catalyst and more preferably greater than 70 wt. %), and the resultant stream 32 is transported to the de-waxing and drying unit 34.

The catalyst separation portion of unit 28 may include a gas disengagement vessel and a catalyst settler. A number of settler designs might be used that collect a dense phase of catalyst particles within a liquid hydrocarbon. For example, the catalyst settler may be a Lamella settler of the type that is used widely in waste treatment plants or a conical vessel with baffles and a hydrocyclone for wax and catalyst separation. The catalyst regeneration can be performed continuously or in batch.

The de-waxer and dryer unit 34 has the purpose of taking the concentrated catalyst and removing wax and drying the catalyst to the point that the volume of wax remaining is equal to or preferably less than the pore volume of the catalyst in the unit 34. Thus, while there is still some wax on the catalyst, it nevertheless becomes a free-flowing powder catalyst that can be fluized. The de-waxing and drying is preferably done with a thermal, mechanical dryer, but could also be done with a solvent wash followed by a milder thermal treatment. "De-waxing" refers generally to removing the liquid constituent and as described below to obtain a free-flowing powder.

A de-waxer/dryer 34 of the thermal-mechanical type typically will have a jacket that is heated with a heating media (e.g., steam or hot oil), a sweep gas that is used to carry away volatized product as well remove additional product, and a mechanical agitator of some type. An electrically heated unit might also be used if desired. The hydrocarbons or wax are removed from the solids by volatilization. A small amount of $O_2$ can be added at the end of the de-waxing step to pre-oxidize the catalyst before transporting it to the fluidization/oxidation step 38.

In the de-waxer/dryer 34 of the thermal-mechanical type, the temperature is raised and an inert gas (e.g., $N_2$) is used as a sweep gas. The sweep gas might may be nitrogen ($N_2$), tail gas (residual gas from the Fischer-Tropsch process that contains typically $C_{5<}$), steam, Ar, $CH_4$, or other relatively inert compositions not containing $O_2$. The sweep gas flow rate will vary with catalyst specifics, but for a cobalt on alumina F-T catalyst, it is preferably greater than 100 GHSV (Gas hourly space velocity) of the total concentrated slurry volume, and more preferably about 1000–9000 GHSV. With a cobalt on alumina slurry F-T catalyst, the temperature is preferably raised to between about 500 and 800 F [260 and 427 C], but other temperatures can be used. The temperature is raised high enough to promote volatilization, but not so high as to cause unwanted side reactions, such as pyrolysis of the hydrocarbons.

The unit 34 volatizes the hydrocarbons (but does not significantly oxidize them) and removes them through vapor transport. The dewaxer/dryer unit 34 is preferably operated at a vacuum or alternatively at a pressure between 1 ATM and 500 psig [101 KPa and 3447 KPa] and more preferably between 1 ATM and 50 psig [101 KPa and 345 KPa]. A temperature high enough to volatize a portion of the wax is used. The dryer operating temperature is the primary variable in setting the amount of wax removal. The $N_2$ (or other inert gas) flow rate and hold time are also important in determining the amount of liquid volatized from the unit 34. Most of the mechanical-thermal dryers will have an outer jacket that is supplied with a heating medium such as steam or specifically formulated heat transfer media, e.g., DOWTHERM 77. The dryer temperature is preferably about 500–800 F [260 and 427 C] and more preferably about 650 F [343 C], but it can vary depending on the heating media (e.g., Dowtherm 77 hot oil and molten salt). The vacuum capability of a dryer should provide an oxygen-free environment in the dryer before applying the heat for safety reasons. Other practices to ensure an oxygen free environment might also be used; for example, a nitrogen purge might be used prior to heating up the dryer. The dryer itself may be a batch mode or a continuous mode unit, depending on the regeneration sequence and cycles.

Another approach is to perform the de-waxing and drying at pressure (preferably one atmosphere). With this approach the de-waxing and drying steps are done at pressure with a suitable amount of inert gas to strip the hydrocarbons from the catalyst surfaces and pores.

The catalyst coming out of unit 34 typically still has some wax, but it is generally less than about 10–12 wt. % and corresponds typically to less than the pore volume of the catalyst. The drying process should occur for an adequate time to allow enough wax to be removed so that it is free flowing as described above. In the laboratory, this has taken about 4 to 8 hours, but it depends on the inert sweep gas rate amongst other operating parameters, such as the extent of gas/solids contact. The important outcome of this part of the processes is that the catalyst is de-waxed/dried sufficiently such that it will not stick and is free flowing, i.e., it can be readily fluidized.

One suitable thermal, mechanical de-waxer/dryer is a modified PORCUPINE® dryer available from Bethlehem Corporation, Bethlehem, Pa. Such devices have been used in other arts such as soil remediation. This type of dryer is a thermal rotary dryer that usually operates at a temperature of at least 650 F [343 C]. This dryer will be described further below in connection with FIG. 2. Another suitable thermal dryer is a paddle dryer such as a Nara Paddle Dryer from KOMLINE-SANDERSON Engineering Corporation, Peapack, N.J. The KOMLINE-SANDERSON unit (Model 1.6W-30 is suitable at the laboratory scale) uses two staggered paddles designed for hot oil flow.

The solvent wash approach to dewaxing and drying uses a $C_5$–$C_9$ stream to dilute the slurry in the unit 34. The dryer then removes the $C_5$–$C_9$ content, which can be done at a relatively low temperature. The catalyst comes out of the solvent wash with less than 10 wt. % wax. At that point it is fluidizable. Solvents such as pure hexane, heptane, pentane can be used. The important criteria for selecting the solvent are the boiling point and solubility in wax. The higher boiling liquids should be soluble in solvent.

The free-flowing catalyst powder 36 is transported to an oxygen-treatment-and-reduction unit 38. Once there, the free-flowing powder catalyst can be fluidized and then treated with oxygen and reduced with a reducing gas. In some instances, the fluidized bed system can first be used to remove additional residual F-T material by heating to higher temperatures (e.g.,>650 F [343 C]). This additional drying step can remove heavy constituents and reduce the total carbon content on the catalyst. The temperature for this additional drying can be as high as 800 F [427 C]; however, the temperature depends upon the catalyst and the impact of pyrolytic decomposition of the residual material being removed.

In the oxygen treatment/reduction unit 38, the catalyst powder is fluidized and treated with an oxygen-containing gas. The treatment that is used to fluidize the bed has a flow rate of at least 1–2 cm/s, but not so high as to cause entrainment of the catalyst (e.g., less that about 10 cm/s). The rate is typically in the range of 3–8 cm/s. The rate, however, is catalyst dependent. The properties which determine acceptable rates are the mechanical strength of the catalyst, catalyst size, and transport disengagement height of the vessel. Any tendencies for catalyst attrition and entrainment are minimized by proper gas and solids management.

The oxygen treatment may be accomplished with one or more of several methodologies that achieve the following objectives: (i) remove residual hydrocarbons and/or carbon rich deposits that accumulate on the FT catalyst and are not readily volatilized during the drying step (the organic constituents or layer refers to residual hydrocarbons and carbon rich deposits); and (ii) re-oxidize any reduced catalytic metals without adversely affecting the dispersion or reducibility of the catalytic components. These objectives are pursued under conditions that minimize unwanted temperature excursions due to the exothermic nature of these reactions.

The oxygen treatment of a deactivated FT catalyst involves several parallel reactions associated with oxidation of the organic material, oxidation of the catalytic metal, pyrolysis of organic material (under limited $O_2$ conditions), and solid state reactions involving metal oxides or carbides of the catalyst that can interact with the support. There are other reactions that may be important in certain cases. For example, steam can be formed if the amount of organic hydrogen and molecular oxygen is relatively high with reference to the gas rate and rate of catalyst oxidation. This steam may interact with the catalyst through a number of reaction mechanisms including gasification and sintering. Additionally, the steam may interact directly with the catalyst support.

During the oxygen treatment, the combustion of hydrocarbons and carbon rich materials competes with the oxidation of any reduced metal. At low temperatures (typically below 450 F. [232 C.]) both reactions may be slow and the oxidation of the metal may be hampered by the organic layer covering the metal (catalytic surface). As the organic layer is removed, the availability of the reduced metal components to the molecular oxygen is increased and oxidation of the metal can proceed more rapidly than that of the organic constituents. The exothermic nature of the metal oxidation can lead to localized high temperatures. These high temperatures combined with limited $O_2$ availability can lead to pyrolysis of a portion of the organic constituents. Pyrolysis products can produce a hard-to-oxidize carbon layer covering the catalyst surface that may impede subsequent reduction. In some cases, the carbon rich products formed during pyrolysis can interact with the metal-to-oxide phase transition occurring during metal oxidation. This interaction may lead to metal oxide phases, which cannot be fully activated in the final reduction step. This results in a loss in the recovered activity of the activated catalyst. Another possibility is that the localized high temperatures can adversely affect the dispersion of the catalytic material by a sintering or agglomeration process.

Accordingly, the preferred oxygen treatment process utilizes the proper combination of $O_2$ flow and temperature to minimize unwanted temperature exotherms and to minimize the amount of residual carbon remaining on the treated catalyst. There are several methodologies that can be employed to accomplish the objectives of the oxygen treatment. These methodologies include three main approaches: (A) Fixed $O_2$ Levels with Ramping Temperature; (B) Fixed Temperature with incremental $O_2$ Level; and (C) Combinations of (A) and (B) above. These methods are discussed in more detail below.

The first approach to oxygen treatment uses fixed $O_2$ levels while ramping the temperature. This method employs a limited amount of $O_2$ in an inert (for example $N_2$ or Ar) and a constant flow rate so that the delivery of oxygen to the catalyst is relatively constant. Typically the amount of oxygen is relatively low (<3 vol %) in commercial operations in order to minimize the potential exotherm and associated temperature rise. The catalyst is initially contacted with the $O_2$ containing gas at a relatively low temperature (typically <350 F [177 C]) and the temperature is increased gradually in order to control the extent of metal oxidation and organic constituent combustion. Typical ramp rates are on the order of 0.5 to 5 F/min [0.3 to 2.8C/min.] depending upon the vessel size. The maximum temperature employed in this method is typically <1100 F [593 C] due to unwanted side reactions resulting in the degradation of properties within the support and/or solid state interactions between the catalytic metal and the support.

The $O_2$ level and ramp rate are important parameters in this approach. Excessive $O_2$ levels (either by using relatively high $O_2$ concentrations or flow rates) can lead to unwanted exotherms resulting in too high a temperature. Ramping at high rates (typically >10 F/min [5.6C/min.]) can lead to the high oxygen consumption rates specifically with respect to the combustion of the organic constituents. If the organic constituents are at a sufficiently high temperature (>600 F [316 C]), they can under go pyrolysis rather than combustion resulting in unwanted carbon rich material depositing on the catalyst surface or within the oxide phase. This oxygen treatment method can also employ stopping the ramp at selected intermediate temperatures in order to allow sufficient $O_2$ to contact the catalyst at low enough temperatures to prevent excessive combustion or oxidation rates later that can lead to oxygen starvation within the catalyst matrix.

The second approach to the oxygen treatment is to use a fixed temperature with incremental $O_2$ levels. In this method, the temperature is fixed at a sufficiently high level to allow both oxidation and combustion to occur simultaneously but at rates that are relatively low (low enough to prevent potentially damaging exotherms within the catalyst matrix). Starting at a sufficiently high temperature (typically >450 F [232 C]), a small amount of $O_2$ (typically less than 1 vol. %) is introduced at a flow rate sufficiently low enough to prevent unwanted exotherms. The $CO_2$ level can be monitored within the exit gas, or off gas, to determine that oxidation is occurring. Monitoring the effluent $O_2$ and $H_2O$ levels permits evaluation of the nature of the carbon oxidation (carbonaceous vs F-T products). Typically when the $CO_2$ level corresponds to less than 20% of that corresponding to complete $O_2$ conversion, one may increase the $O_2$ level in the feed. In a series of steps the $O_2$ level is increased to a maximum absolute value (up to 40% $O_2$ in the treatment gas). The step of each increment is preferably on the order of a 0.5–4% absolute increase in the $O_2$ content. The timing of each $O_2$ increment can correspond to a decrease in the effluent $CO_2$ level indicating that the oxidation rate is descreasing. The rate of O2 increase should depend upon the $CO_2$ level. As the $CO_2$ level in the effluent gas increases to the level corresponding to complete oxygen depletion, the temperature ramping should be preferably decreased. The method involves incrementing the temperature at sufficiently slow rate to prevent complete use of the oxygen. The oxygen conversion should be <100% and preferably <20% conversion of incoming $O_2$.

This second oxygen-treatment method offers the advantage of controlling the oxidation rate at temperatures where both oxidation and combustion will occur simultaneously. The limited oxygen present at the onset of the treatment prevents excessive exotherms during the initial oxidation/combustion periods where the reaction can be the fastest. An important parameter in this method is the temperature at which the reduced metal undergoes oxidation. The desired process temperature must be above the oxidation temperature for the specific catalyst system being treated.

The third approach to the oxygen treatment is to combine aspects of the first two methods. In this combined method, the oxygen treatment involves incrementing $O_2$ to a specified level at a fixed temperature in order to allow oxidation and combustion to occur. This temperature is in the range of 400–600 F [204–316 C] in order to allow combustion of residual hydrocarbons to occur. Upon reaching a specified $O_2$ level, the temperature is ramped to a higher temperature. After holding at the higher temperature, the $O_2$ level is increased in time increments corresponding to low rates of oxidation. The $O_2$ level is preferably increased in 0.5 to 4% absolute increments when the effluent $CO_2$ levels signify a very low extent of oxidation (typically less than 80%, preferably less than 20%, of the incoming $O_2$).

The third approach allows for the combustion of residual hydrocarbons and oxidation of the F-T catalyst to occur under conditions that minimize potential exotherms. The oxidation occurs under controlled conditions that minimize unwanted temperature excursions. Upon completion of hydrocarbon combustion and possibly re-oxidation of reduced catalyst, the catalyst can be subjected to higher $O_2$ levels and temperatures.

After treating the free-flowing catalyst with oxygen, the catalyst is reduced using a reducing gas such as hydrogen. In reducing the catalyst powder, there are five variables that are considered: (1) reduction pressure; (2) flow rate, which is measured as total volume of reduction gas per volume of catalyst per hour, or volumes of reduction gas per hour or a gas hourly space velocity (GHSV); (3) reduction temperature; (4) the reduction temperature ramp rate; and (5) the percentage hydrogen in the reduction gas. There are many permutations that can be used to adequately reduce the catalyst. Two examples that are believed appropriate for base work in the laboratory (A) and believed appropriate for a commercial operation are as follows:

|  | A | B |
|---|---|---|
| Flow | 6000 GHSV | 1000 GHSV |
| Reduction Pressure | 50 psig [345 KPa] | 500 psig [3447 KPa] |
| Reduction temp | 650 F. [343 C.] | 750 F. [399 C.] |
| Reduction Ramp Rate | 0.1 F./min. [0.06 C./min] | 1 F./min. [0.6 C./min] |
| % H2 in reduction gas | 100 | 50 |
| Holding Time at temp. | 2 hours | 24 hours |

The reduction is carried out in a fluidized bed. It may be possible to use less than 100% $H_2$; for example, with a cobalt-based F-T catalyst, the required hydrogen is dependent on the amount of cobalt oxides available and the gas-solid contacting efficiency in the reduction step. The fluid bed will have a gas velocity ($U_g$) that is preferably as follows: 2 cm/s<$U_g$<13 cm/s. The flow of reducing gas will be continued as long as necessary, but is preferably greater than 4 hours. The process variables set in conditions A and B represent the range of acceptable values where adequate activity is obtained during reduction.

Referring again to FIG. 1, the regenerated catalyst powder 40 is transported to the re-slurry unit 42 where it is re-slurried. The free-flowing catalyst is mixed in unit 42 with wax to re-slurry it. It also heated up to at least 350 F [177 C] or to approximately the same temperature as the slurry F-T reactor 24 prior to introduction of the regenerated slurry catalyst into the F-T reactor 24. New catalyst can also be added to system 10 at the re-slurry unit 42. The resultant regenerated slurry catalyst 44 is returned to the slurry Fischer-Tropsch reactor 24.

Referring to FIG. 2, another illustrative embodiment of a system 100 for converting light hydrocarbons into heavier hydrocarbons is presented that includes a slurry F-T regeneration subsystem. A synthesis gas generator 102 receives light hydrocarbons 104, steam 106, and an oxygen-containing gas 108 and prepares a synthesis gas.

The synthesis gas is delivered by conduit 110 to a slurry Fischer-Tropsch reactor 112. Reactor 112 will include a means for creating the proper flow within the reactor such as a distributor 114. An overhead F-T product stream or light product stream is removed through conduit 116. A slurry stream is pulled from the F-T reactor 112 by a weir 118 and a slurry removal conduit 120. The slurry stream is used for catalyst concentration and further product removal.

The slurry in conduit 120 is delivered to a gas disengagement vessel 122. The gases, which contain $H_2$, CO, $N_2$, and $CO_2$, are released and delivered by conduit 124 to be processed with the reactor effluent of conduit 116. The FT exit gas of conduit 116 is cooled by heat exchanger 126 before delivery to an F-T overhead accumulator 128, which collects the hydrocarbon products that condense when cooled. The light overhead can be used as a fuel through out the system 100 and can be used for power generation amongst other possible uses. The de-gassed slurry goes to conduits 130 and 132.

The degassed slurry stream in conduit 130 goes to a product removal device 134, e.g., a cross-flow filter, where product can be pulled off (without undue catalyst fines) into F-T product stream 136. The remaining portion of the slurry stream exiting device 134 is delivered by conduit 138 to return conduit 140.

The portion of the de-gassed slurry delivered to conduit 132 passes through a pressure letdown valve 142 into catalyst settler 144. In this embodiment, the disengagement vessel 122, filter 134, and settler 144 make up a product removal and catalyst separation subsystem. Catalyst settler 144 produces a concentrated catalyst portion 146 that is delivered by conduit 148 to a de-waxing/drying unit 150.

The catalyst to be regenerated is preferably re-generated in batches pulled on a schedule, but continuous processing systems are possible. With valve 149 open and valve 153 closed on conduit 151, the catalyst is delivered to de-waxing/dryer 150. A load cell (not shown) can be used in vessel 182 to allow a determination of the approximate catalyst mass that has been removed from reactor 112 and to thereby assist with mass balance considerations. The catalyst can be removed on a schedule to allow for regeneration to occur as needed to keep the catalyst in reactor 112 with sufficient activity; for example, with a commercial-size plant, the withdraw rate can be 2 to 10% per week (based on a typical decay rate). Catalyst settler 144 may include measuring devices and controls to keep a sufficient level of slurry in it. At any given time when the desired amount of catalyst has been removed by conduit 148 and delivered to the dryer 150, valve 149 may be closed and valve 153 open; in this configuration, the concentrated catalyst from settler 144 will be returned by conduits 155, 140 to reactor 112.

A liquid 152 with reduced catalyst content is prepared in settler 144 and delivered to conduit 154. The liquid stream of conduit 154 may be used as a product off take, in which case it is delivered by conduit 156 to a polishing filter 158 and then on through conduit 160 to storage or to upgrading, or it can go for use in re-slurrying the regenerated catalyst powder, which is discussed further below. In the latter case, the stream is delivered by conduit 162 to conduit 164, which delivers it to slurry mixing vessel 166.

Another stream is removed from settler 144 and delivered by conduit 145 to wax separator 176. Stream 145 is a hydrocarbon vapor produced during the settling and potential flashing that results when the pressure in the separator 144 is significantly lower than the reactor 112. The stream from conduit 145 as well as that from conduit 174 (described below) are separated in wax separator 176. The light ends in separator 176 go through conduit 177 to F-T overhead accumulator 128 and heavier liquids go through conduit 164 to slurry mixing vessel 166 to re-slurry the regenerated catalyst.

Figure 3:
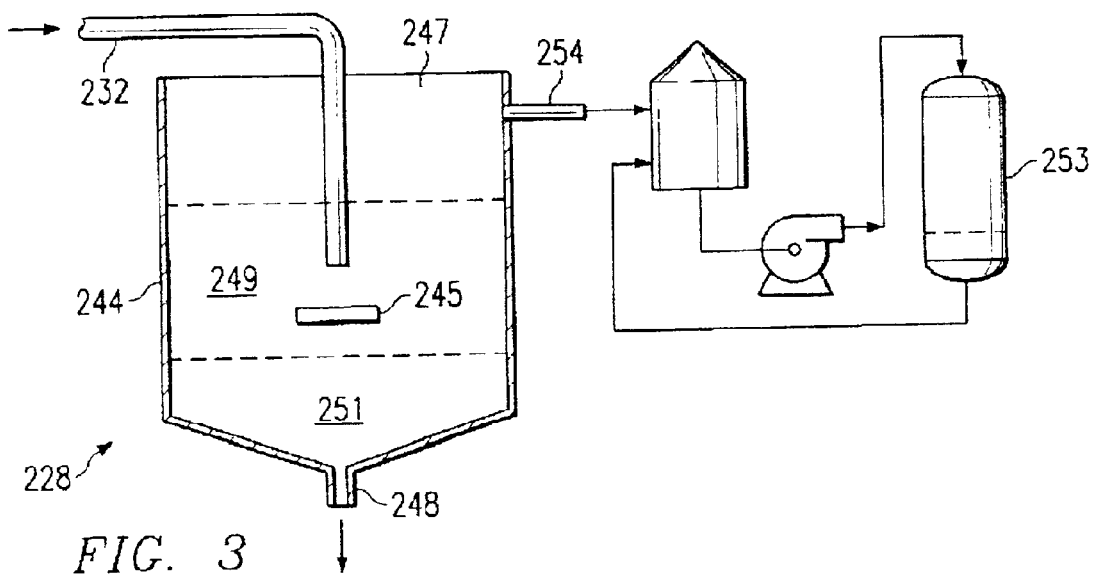
FIG. 3 is an embodiment of a catalyst separation unit suitable for use as an aspect on one embodiment of the present invention.

Referring to FIG. 3 another embodiment of a catalyst separation unit 228 that might be used with system 100 is presented. The slurry catalyst is delivered by conduit 232 from the reactor to the unit 228. The catalyst pulled from the weir (e.g., 118 in FIG. 1) in conduit 232 has roughly 30–40 wt. % of catalyst. It is delivered to the conical settler 244 and initially impinges on plate 245. The interior of settler 244 may be thought of as having three zones: a clear zone 247, a settling zone 249, and a settled zone 251. Product is pulled from clear zone 247 through conduit 254. The product in conduit 254 may have remaining catalyst in it, e.g., on the order of 3 wt. %. That remaining catalyst may be removed by a cross-flow filter 253 or other devices such as centrifugal unit.

The catalyst that settles into zone 251 will drop down the sloped walls (preferably sloped at about 20 degrees) to conduit 248. Conduit 248 will deliver the catalyst to the drier. The catalyst in conduit 248 probably has about a 60–70 wt % concentration.

Referring back to FIG. 2, the concentrated slurry of conduit 148 is delivered to de-waxing/drying unit 150. This unit 150 is used to dry the catalyst so it will be fluidizeable (e.g., catalyst becomes a free-flowing powder catalyst). This is accomplished by removing a sufficient quantity of wax such that the volume of wax remaining (Vr) is generally less than the cumulative pore volume (Vc) of the catalyst in unit 150, i.e., Vr<Vc. There are a number of techniques for doing this as described in connection with FIG. 1.

The preferred method is to use a drying unit that uses thermal energy with mechanical mixing to heat and remove wax with a purging gas. The mechanical mixing should involve relatively low energy in order to minimize catalyst attrition. One suitable type of dryer is a PORCUPINE dryer. While this general type of dryer is known in related arts, a general description of a PORCUPINE dryer follows.

The PORCUPINE dryer includes a main body (jacketed vessel), where the slurry is loaded, one or more agitators located horizontally across the interior of the main body, a gas distributor at the bottom of the main body, a motor or other motive force for the agitator, and a product discharge or collector. In a typical operation of the PORCUPINE dryer, the slurry is loaded and the agitator is activated at about 10–15 RPM. The sweep gas is injected along the bottom to improve the gas-slurry contacting and to maximize the drying efficiency. The gas rate should be set as high as possible to facilitate drying. The upper limit is typically set by that which does not result in significant catalyst carry over or attrition. The sweep or drying gas can be any gas that does not react adversely with the catalyst, such as $N_2$, Ar, $CH_4$, or other relatively inert compositions not containing $O_2$. Heat is applied from a hot oil subsystem that delivers hot oil to the agitator and the jacket of the main body. After the desired temperature is reached, the temperature is held for a set time (e.g., 4–6 hours) until there is no significant wax recovery in the product receiver. The wax vapor generated in the process is recovered through a quench exchanger and the product receiver at regular intervals during the drying and de-waxing process. The drying efficiency of the PORCUPINE dryer is primarily dependent on the operating temperature, wax content in the slurry, agitation speed, sweep gas rate, and distribution along the bottom. The sweep gas rate may be adjusted during operation at different times in the cycle. For example, as the catalyst becomes dryer, it may be necessary to lower the sweep gas rate to avoid entrainment.

Figure 4:
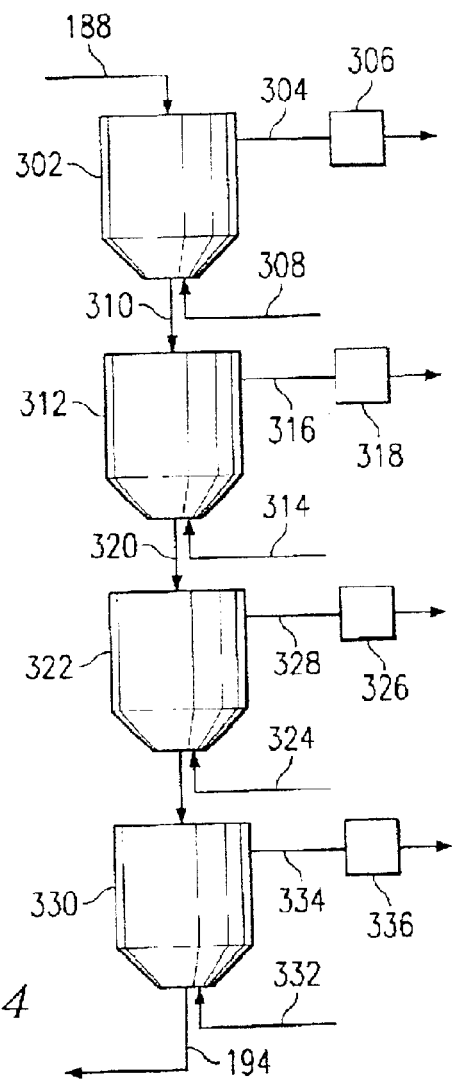
FIG. 4 is an embodiment of an oxygen-treatment-and-reduction unit of a system for regenerating a slurry Fischer-Tropsch catalyst.

Returning to the specific description of the embodiment, the temperature is preferably raised to about 650 F [343 C] in the PORCUPINE dryer. Higher or lower temperatures (400–800 F [204–427C]) can be employed depending upon the nature of the catalyst and liquids to vaporized. The removed vapors are carried away by conduit 170, which includes heat exchanger 172. Any condensed liquid products can be delivered by conduit 174 to wax separator 176 and the remaining gas effluent may be used in a combustor. The purge gas, or sweep gas, is supplied by conduit 178 and is preferably about 0.1 to 10 standard cubic feet (scf) [0.0028 to 0.2832 standard cubic meter] of inert gas per pound [~0.45 Kg] of slurry, or more preferably 1–3 scf [0.028–0.085 scm] of inert gas per pound [~0.45 Kg] of slurry. The free-flowing, powder catalyst is delivered to catalyst hopper and loading cell 182. From there, the powdered catalyst is delivered pneumatically to the oxygen-treatment-and-reduction vessel 186 by conduit 188. While vessel 186 is shown and described as a single vessel, it may be two separate, but connected, vessels (or more as shown in FIG. 4).

When the catalyst arrives at de-waxer/dryer 150 it probably has about 60–70 wt. % catalyst (30–40 wt. % hydrocarbon product). A significant portion of the product with the catalyst is removed in the dryer, but not all. There is still probably something on the order of about 10–15 wt. % of product when the catalyst is delivered to vessel 186. Once, there it may be burned to remove some more.

Upon arriving at oxygen-treatment-and-reduction vessel 186, the powder may be fluidized with gas from a gas-supply conduit 189 and then heated to temperatures higher than those that were reached in the dryer 150, e.g., it may be raised to as high as 1000 F [538 C] or as high as can be achieved without unwanted reactions taking place in the catalyst metal or support. The temperature is raised by flowing an inert (e.g., nitrogen or argon or other gas that does not change the catalyst characteristics). The flow velocity is preferably in the range of 2–13 cm/sec to ensure that the particles are fluidized but not entraining out of vessel 186. Consider for example, the additional heating with nitrogen described in Example 3 below. This oxidation step removes additional wax through conduit 190. Conduit 191 carries wax away for particle fine removal and then on to storage or for other uses. This stream can also be recycled to the gas inlet of vessel 186 by a recycle conduit, e.g., conduit 192 that delivers it to gas supply line 189.

The powdered catalyst is then put through an oxygen treatment of the type described in connection with FIG. 1 and below in connection with Examples 1 or 2. The various approaches to knowing the end-point of the oxidation were discussed in connection with FIG. 1, but note that the $CO_2$ produced during the process can be measured by $CO_2$ analyzer 193 and the resultant information used to stage the variation in $O_2$ if that approach is used.

After the powdered catalyst has been treated with an oxygen-containing gas to the point that a sufficient amount of wax and contaminants have been removed, the reduction process with a reducing gas is started. Monitoring the $CO_2$ content of the effluent with analyzer 193 during the oxygen treatment allows one readily to determine when a sufficient amount of carbon has been removed. The $CO_2$ content may be correlated to the wax remaining on the catalyst. The wax remaining can be determined by analyzing the catalyst for loss of ignition (LOI). The temperature of the catalyst can also be monitored for information on when all oxidation is complete—a temperature drop in the oxygen treatment indicates that the process is complete. A moisture analyzer 197 may also be used as another indication of when the reduction treatment is complete.

The reduction is preferably accomplished as the reduction is described in connection with FIG. 1. Once the catalyst powder is reduced, the powder is delivered by conduit 194 to slurry mixing vessel 166, where it is mixed with wax from conduit 164 to re-slurry it. Gas supply conduit 195 supplies an inert gas to keep the slurry suspended. The catalyst should not settle to the bottom of the vessel 166. Conduit 195 is also used to pressurize vessel 166 to transfer the slurry to reactor 112. The regenerated slurry may be heated to approximately the same temperature as the slurry that is already in F-T reactor 112. From there, the regenerated, slurry catalyst is delivered by conduit 196 to return conduit 140 and into slurry reactor 112. In this embodiment, the regeneration subsystem includes degasser 122, settler 144, dewaxer/dryer 150, $O_2$-treatment-and-reducing unit 186, and a slurry mixer 166.

It was noted earlier that vessel 186 could in practice involve a plurality a vessels, and now such a system is presented in connection with FIG. 4. The fluidizable catalyst is delivered by conduit 188 from the dryer 150 to the drying/oxygen-treatment vessel 302. There it maybe dried and then oxidized. The oxygen-containing gas is delivered by conduit 308. The off-gas is delivered to conduit 304, which may contain a CO2 analyzer 306. Once oxidation is completed there, it may be feed (pneumatically or by gravity) through conduit 310 to reduction vessel 312.

In vessel 312, the catalyst is reduced with a hydrogen gas delivered through conduit 314. The off gas is delivered to conduit 316, which contains a humidity (dew point) analyzer 318. The reduction process produces moisture early on and so the humidity may be used to gauge the extent of reduction. Once a reduction is completed, the catalyst may be feed through conduit 320 to oxygen-treatment vessel 322. There an oxygen-containing gas is delivered through conduit 324 to further oxidize the catalyst. A CO2 analyzer 326 on off-gas conduit 328 may be used gauge the extent of oxidation. Once oxidation is complete, the catalyst may be feed to second reduction vessel 330.

In reduction vessel 330, hydrogen is feed through conduit 332 to further reduce the catalyst. The humidity of the off-gas in conduit 334 may be monitored by a humidity analyzer 336. Once reduction is complete, the regenerated catalyst may be delivered to conduit 194 for return to the reactor 112. Note this embodiment of the oxygen-treatment-and-reduction unit shows four vessels but the patter could be repeated as desired or reduced to just two vessels or one vessel (FIG. 2).

Referring against to FIG. 2, note that hydrogen treatment steps may be added at a number of locations in system 100. In one embodiment, a hydrogen treatment could be performed on conduit 148 with an upward gas flow through the catalyst settler 152 before conducting the drying step. One might also do it after drying it but before the oxygen treatment in vessel 186.

EXAMPLE 1
Ramped Oxygen Treatment

An example procedure based on an illustrative run at laboratory scale (laboratory scale fluidized bed reactor) is now presented. This example used the ramped oxygen approach to performing the oxygen treatment. It is not intended to be limiting in any way, but presented merely as an example.

Spent catalyst, which had 900–1200 hours of service, was placed in a ½ inch [1.27 cm] fluidized bed vessel. The treatment was done very conservatively with respect to how high temperature was allowed to go. In this instance a cobalt on alumina slurry F-T catalyst was regenerated by the following steps. The catalyst sample, which was cobalt on alumina, was loaded at 100 F. The temperature was ramped from 100 F [38 C] to 600 F [316 C] at 1 F/ minute [0.6 C/min.] under $N_2$ at 6000 GHSV and 50 psig [345 KPa] and held 4 hours. The catalyst was then cooled to 575 F [302 C] at 1 F/minute [0.6 C/min.]. An oxygen-containing gas was then flowed with the oxygen at 0.5% and the $CO_2$ level monitored. When the $CO_2$ dropped below 1000 ppm, the $O_2$ was brought to 1%. When $CO_2$ dropped to about 700 ppm, the $O_2$ was increased to 2%. When the $CO_2$ dropped to less than 500 ppm, the temperature was increased to 700 F [371 C] at 1 F/minute [0.6 C/min.]. When the $CO_2$ dropped to about 200 ppm, the temperature was increased to 800 F [427 C] at 1 F/minute [0.6 C/min.]. When the $CO_2$ dropped to about 400 ppm, the oxygen was increased to 5%. When the $CO_2$ again dropped to less than 500 ppm, the oxygen was increased to 10%. When the $CO_2$ again dropped to less than 500 ppm, the oxygen was increased to 14%. When the $CO_2$ again dropped to about 500 ppm, the oxygen was increased to 17%. When the $CO_2$ again dropped to about 500 ppm, the oxygen was increased to 21% and held until the $CO_2$ off gas reached <100 ppm. The catalyst was then reduced with hydrogen.

This conservative approach of doing an oxygen treatment was followed by reduction and was found to do a good job of regenerating the catalyst sample. The regenerated catalyst was tested in a CSTR and found to have about a 48–52% CO conversion at 6000 GHSV, 410 F [210 C], and a gas composition of 34% $H_2$, 17% CO, balance $N_2$. Analysis of the catalyst shows that the catalyst that has been subjected to incremental $O_2$ treatment has improved dispersion and reducibility. Both of these properties improve catalyst performance.

EXAMPLE 2
Constant Oxygen Treatment

One illustrative example of a laboratory scale regeneration of a cobalt on alumina slurry F-T catalyst using a constant oxygen concentration is presented. The vessel used was the same as in Example 1. The example is not intended to be limiting, but to just present one possible example at this scale. The following steps were used. The slurry catalyst was loaded into the regeneration vessel at 100 F. The temperature was ramped from 100 F to 600 F [38–316 C] at 1 F/minute [0.6 C/min.] under $N_2$ at 6000 GHSV and 50 psig [345 KPa] and held for 2 hours. The catalyst was then cooled to 300 F [149 C] at 1 F/minute [0.6 C/min.]. At this point, the gas was switched to 2% $O_2$, 6000 GHSV, 50 psig [345 KPa] and the temperature was ramped to 575 F [302 C] at 1 F/minute, and conditions held for 8 hours. The catalyst was then cooled to 300 F [149 C]. After this the catalyst was reduced by switching to 100% $H_2$, 6000 GHSV, 50 psig, ramp to 650 F [343 C] at 1 F/minute [0.6 C/min.] and held 8 hours. The regenerated catalyst demonstrated good performance after regeneration.

EXAMPLE 3
High Temperature Inert Gas Treatment for De-Waxing and Drying

In this example, deactivated cobalt catalyst (4000 hours of operation time) was dried as previously referenced and then was also treated with 650 F [343 C] nitrogen. The catalyst was then given a 2% (vol.) oxygen treatment at 575 F [302 C]. Then a 100% hydrogen treatment was performed at 650 F [343 C]. The catalyst recovered nearly 100% of its original activity. The inert gas in this example is believed to remove as much wax as possible prior to the oxygen treatment to reduce the amount of residual hydrocarbons on the catalyst surface or pores. This inert treatment that was added before the oxygen treatment helps to reduce the time required for the oxygen treatment and increases the product recovery.

Although the present invention and its advantages have been described in detail, it should be understood that various changes, substitutions and alterations can be made therein without departing from the spirit and scope of invention as defined by the appended claims.

What is claimed is:

1. A process for regenerating a slurry Fischer-Tropsch catalyst that needs regeneration, the process comprising the steps of:
   separating the catalyst from the slurry;
   de-waxing and drying the catalyst sufficiently to produce a free-flowing catalyst powder that is fluidizable;
   fluidizing the catalyst powder;
   treating the catalyst powder with an oxygen treatment (oxidizing);
   reducing the catalyst powder with a reducing gas to form a reduced catalyst powder; and
   mixing the reduced catalyst powder with hydrocarbons to form a regenerated, slurry catalyst.

2. The process of claim 1 wherein the steps of treating the catalyst powder with an oxygen treatment and the step of treating the catalyst powder with a reducing gas comprise the following steps:
   (A) treating the catalyst powder with an oxygen treatment;
   (B) treating the catalyst powder with a reduction gas;
   (C) treating the catalyst powder again with an oxygen treatment; and
   (D) treating the catalyst powder again with a reduction gas.

3. The process of claim 2 wherein a pattern of (A) oxygen treatment, (B) reductions (C) oxygen treatment, and (D) then reduction is repeated until a desired level of catalyst activity is restored or no further catalyst activity is recovered.

4. The process of claim 1 wherein the step of treating the catalyst powder with an oxygen treatment comprises the steps of setting a temperature and holding the temperature, flowing an oxygen containing gas over the catalyst; and increasing the oxygen content of the oxygen-containing gas.

5. The process of claim 1 wherein the step of treating the catalyst powder with an oxygen treatment comprises the steps of flowing an oxygen-containing gas over the catalyst; increasing the temperature at a rate of 0.1 to 2 F/mm. [0.06 to 1.11 C/mm.] until reaching a hold temperature in the range of 450–900 F [232–482 C]; and holding at the hold temperature for 4–24 hours.

6. The process of claim 1 wherein the step of treating the catalyst powder with an oxygen treatment comprises the steps of flowing an oxygen-containing gas over the catalyst; increasing the temperature to a hold temperature while maintaining $CO_2$ effluent rates at values corresponding to complete usage of incoming oxygen; and holding at the hold temperature in the range of 450–900 F [232–482 C] for 2–24 hours.

7. The process of claim 1 wherein the step of treating the catalyst powder with an oxygen treatment comprises the steps of setting a temperature between 450–900 F [232–482 C]; flowing an oxygen-containing gas over the catalyst; and increasing the oxygen content of the oxygen-containing gas from about 2 volume percent to 21 volume percent in increments that do not provide for complete combustion of oxygen as determined by measuring the $CO_2$ in an off gas.

8. The process of claim 1 further comprising the step of monitoring the $CO_2$ level of an off gas from the oxygen treatment and wherein the step of treating the catalyst powder with an oxygen treatment comprises treating the catalyst powder with an oxygen-containing gas in which the oxygen content is systematically increased up to about 21 vol. % or higher and held until the $CO_2$ off gas is less than 100 ppm.

9. The process of claim 1 further comprising the step of monitoring the $CO_2$ level of an off gas from the oxygen treatment and wherein the step of treating the step of treating the catalyst powder with an oxygen treatment comprises treating the catalyst powder with an oxygen-containing gas in which the oxygen content is held at a level below 5 vol. % until the $CO_2$ off gas is less than 100 ppm.

10. The process of claim 1 wherein the step of de-waxing and drying the catalyst comprises the step of using a mechanical, thermal dryer to de-wax and dry the catalyst.

11. The process of claim 10 wherein the mechanical, thermal dryer operates in a temperature range of 450–800 F [232–427 C].

12. The process of claim 1 wherein the step of de-waxing and drying the catalyst comprises the step of using a solvent wash to de-wax the catalyst and then drying the catalyst.

13. The process of claim 10 wherein the step of drying the catalyst further comprises using a sweeping gas.

14. The process of claim 13 wherein the sweeping gas is nitrogen.

15. The process of claim 13 wherein the sweeping gas is argon.

16. The process of claim 13 wherein the sweeping gas is steam.

17. The process of claim 13 wherein the sweeping gas is a tail gas and methane ($CH_4$).

18. The process of claim 1 wherein the steps of treating the catalyst with an oxygen-containing gas and treating the catalyst with a reducing gas are repeated.

19. The process of claim 1 further comprising the step of treating the catalyst immediately after drying the catalyst with oxygen to partially oxidize the catalyst before treating the catalyst with an oxygen-containing gas while fluidized.

20. The process of claim 1 further comprising the step of stripping hydrocarbons from the catalyst with hydrogen before or after the drying step.

21. An oxygen treatment method for treating (oxidizing) a Fischer-Tropsch catalyst in need of regeneration with oxygen before reducing the catalyst, the treatment method comprising the steps of:
   fluidizing the catalyst;
   flowing an oxygen containing gas over the catalyst; and
   setting a temperature above 100 F [38 C].

22. The process of claim 21 wherein the oxygen-containing gas has a fixed $O_2$ level and further comprising the step of increasing the temperature.

23. The process of claim 21 wherein the temperature is systematically raised and then held at a temperature greater than 500 F [260 C] and systematically increasing the $O_2$ level in the oxygen-containing gas.

24. A process for regenerating a slurry Fischer-Tropsch catalyst that needs regeneration, the process comprising the steps of:

(A) separating the catalyst from the slurry using a settler, (B) using a mechanical, thermal dryer to de-wax and dry the catalyst sufficiently to produce a free-flowing catalyst powder that us fluidizable;

(C) fluidizing the catalyst powder from step (B);

(D) oxidizing the catalyst powder;

(E) reducing the catalyst powder with a reducing gas to form a reduced catalyst powder;

(F) repeating steps (D) and (E) until a desired level of activity is achieved for the catalyst or until no further activity is recovered; and (G) mixing the reduced catalyst powder with hydrocarbons to form a regenerated, slurry catalyst.

* * * * *